(12) United States Patent
Neubardt

(10) Patent No.: US 8,348,983 B2
(45) Date of Patent: Jan. 8, 2013

(54) SURGICAL BONE SCREW CONSTRUCTION

(75) Inventor: Seth L. Neubardt, Mamaroneck, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 780 days.

(21) Appl. No.: 12/077,871

(22) Filed: Mar. 21, 2008

(65) Prior Publication Data
US 2009/0125072 A1     May 14, 2009

Related U.S. Application Data

(60) Provisional application No. 61/002,852, filed on Nov. 13, 2007.

(51) Int. Cl.
*A61B 17/04* (2006.01)
(52) U.S. Cl. ........ 606/304; 600/372; 600/373; 600/377; 606/129; 606/305
(58) Field of Classification Search .................. 606/377, 600/372, 373; 606/129, 300–331
See application file for complete search history.

(56) References Cited

U.S. PATENT DOCUMENTS

| | | | |
|---|---|---|---|
| 4,713,506 A * | 12/1987 | Klink | 200/507 |
| 5,196,015 A | 3/1993 | Neubardt | |
| 5,474,558 A | 12/1995 | Neubardt | |
| 6,010,516 A | 1/2000 | Hulka | |
| 6,391,005 B1 * | 5/2002 | Lum et al. | 604/117 |
| 6,530,926 B1 | 3/2003 | Davison | |
| 6,778,861 B1 * | 8/2004 | Liebrecht et al. | 607/116 |
| 7,207,949 B2 | 4/2007 | Miles et al. | |
| 7,218,232 B2 | 5/2007 | DiSilvestro et al. | |
| 7,470,236 B1 | 12/2008 | Kelleher et al. | |
| 7,522,953 B2 | 4/2009 | Kaula et al. | |
| 7,582,058 B1 | 9/2009 | Miles et al. | |
| 7,657,308 B2 | 2/2010 | Miles et al. | |
| 7,664,544 B2 | 2/2010 | Miles et al. | |
| 7,691,057 B2 | 4/2010 | Miles et al. | |
| 7,693,562 B2 | 4/2010 | Marino et al. | |
| 7,785,253 B1 | 8/2010 | Arambula et al. | |
| 7,819,801 B2 | 10/2010 | Miles et al. | |
| 7,892,173 B2 | 2/2011 | Miles et al. | |
| 7,905,840 B2 | 3/2011 | Pimenta et al. | |
| 7,920,922 B2 | 4/2011 | Gharib et al. | |

(Continued)

OTHER PUBLICATIONS

SYNTHES GmbH, Cannulated Pangea Pedicle Screws, Technical Guide (2007).

*Primary Examiner* — Thomas Barrett
*Assistant Examiner* — Melissa A Golob
(74) *Attorney, Agent, or Firm* — Dilworth & Barrese, LLP

(57) ABSTRACT

A surgical bone screw includes an elongate body having a proximal end, a distal end, a threaded portion on the circumference of the body, and a passage extending between the proximal and the distal ends of the body. An electrical conductor is disposed in the passage between the proximal and the distal ends of the screw body. The conductor has a first terminal at the proximal end and a second terminal at the distal end. The conductor and both of the terminals are electrically insulated from surrounding portions of the screw body. When the screw is driven into bone tissue and a stimulating current is applied to the first terminal, the current is directed substantially through the conductor to flow into tissue adjacent to the second terminal at the distal end, without shunting by other tissue that surrounds the screw body.

20 Claims, 5 Drawing Sheets

U.S. PATENT DOCUMENTS

| | | |
|---|---|---|
| 7,935,051 B2 | 5/2011 | Miles et al. |
| 7,942,826 B1 | 5/2011 | Scholl et al. |
| 7,962,191 B2 | 6/2011 | Marino et al. |
| 7,963,927 B2 | 6/2011 | Kelleher et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,016,767 B2 | 9/2011 | Miles et al. |
| 8,027,716 B2 | 9/2011 | Gharib et al. |
| 8,050,769 B2 | 11/2011 | Gharib et al. |
| 8,055,349 B2 | 11/2011 | Gharib et al. |
| 2004/0243207 A1* | 12/2004 | Olson et al. ............ 607/116 |
| 2005/0010300 A1* | 1/2005 | Disilvestro et al. ........ 623/18.12 |
| 2005/0182454 A1 | 8/2005 | Gharib et al. |
| 2006/0173374 A1 | 8/2006 | Neubardt et al. |
| 2006/0173456 A1* | 8/2006 | Hawkes et al. ............ 606/61 |
| 2006/0173521 A1 | 8/2006 | Pond, Jr. et al. |
| 2006/0178593 A1 | 8/2006 | Neubardt et al. |
| 2006/0178594 A1 | 8/2006 | Neubardt et al. |
| 2006/0200023 A1 | 9/2006 | Melkent et al. |
| 2008/0125637 A1* | 5/2008 | Geist et al. ............ 600/372 |
| 2008/0262526 A1* | 10/2008 | Neubardt et al. ............ 606/180 |
| 2009/0125072 A1 | 5/2009 | Neubardt |
| 2010/0094115 A1 | 4/2010 | Pond, Jr. et al. |

* cited by examiner

SURGICAL BONE SCREW CONSTRUCTION

CROSS REFERENCE TO RELATED APPLICATION

This application claims priority under 35 U.S.C. §119(e) of U.S. Provisional Patent Application No. 61/002,852 filed Nov. 13, 2007, and entitled Surgical Pedicle Screw Construction.

BACKGROUND OF THE INVENTION

1. Field of the Invention

The present invention concerns surgical implants, particularly bone screws.

2. Discussion of the Known Art

U.S. Pat. No. 5,474,558 (Dec. 12, 1995) discloses a procedure and system for spinal pedicle screw insertion, wherein pedicle screws can be inserted into vertebrae of the spine in a way that reduces the likelihood of nerve damage due to improper screw placement. See also U.S. Pat. No. 5,196,015 (Mar. 23, 1993). Basically, as a screw opening is formed in the pedicle, an electric potential is applied to the inside wall of the opening while the patient is observed for a nervous reaction such as, e.g., leg twitching. Formation of the opening is continued while the electric potential is applied, until a desired hole depth is obtained without monitoring a nervous reaction. If a reaction occurs, the direction in which the opening was then being formed, is changed. The mentioned '558 and '015 U.S. patents, and U.S. Patent Application Pub. No. 2006/0173374 (Aug. 3, 2006), disclose a system and tools for carrying out the foregoing procedure.

Conventional pedicle screws available from, e.g., Biomet, Inc., of Warsaw, Ind., and SpineUniverse, LLC, of Montclair, N.J., are made from titanium, stainless steel, or other strong medical grade alloy. The screws are typically provided with so-called polyaxial or mobile cup-shaped head extensions for seating and locking associated rods once the screws are properly located and driven into the spine. The screw heads usually have hexagonal or slotted recesses for receiving a matching drive tool bit.

An expandable screw for spine fixation offered by Biomet, Inc., under the mark Biomet® Omega21™, is cannulated to accept an expansion peg. A lower (distal) threaded portion of the screw body is formed into four quadrants or fins that expand radially outward to lock the screw in bone tissue when the peg is inserted through a central passage in the screw. Withdrawing the peg allows the fins to collapse for easy removal of the screw when necessary, according to the manufacturer.

Other cannulated screws available from Synthes®, Inc., of West Chester, Pa. and identified as Pangea® pedicle screws, have central bores that are open at both ends of the screws. To insert a screw into bone, the tip of a guide (Kirschner) wire is first seated at a certain depth in a spinal pedicle using a cannulated awl. The awl is removed, and a pedicle probe is guided over wire to prepare a screw channel. After an optional channel threading step, the free end of the wire is inserted through the bore of a selected pedicle screw, and the screw is driven 2-3 rotations into the bone using a cannulated screwdriver shaft. The wire is then removed, and the screw driven further to a desired depth in the bone. A tutorial on use of the Synthes cannulated screws is available on the Internet at <http://www.synthes.com/site/fileadmin/Shared/shop/Printed_Materials/Techique_Guide/Spine__2007__08/036.000.941.pdf>.

U.S. Pat. No. 7,218,232 (May 15, 2007) discloses a bone fastener having a threaded engaging portion and a head portion. In one embodiment, the fastener has a cavity formed in the head portion, and a storage device such as a RFID tag is embedded in the cavity. According to the patent, the device may carry information that is specific to both the fastener and the patient.

There remains a need for a bone screw that is constructed to cooperate with the earlier mentioned systems and tools, and thus reduce substantially the possibility of nerve damage resulting from an improperly placed screw.

SUMMARY OF THE INVENTION

According to the invention, a surgical bone screw includes an elongate screw body having a proximal end, a distal end, a threaded portion on the circumference of the body, and a passage extending between the proximal and the distal ends of the body. An electrical conductor is disposed in the passage between the proximal and the distal ends of the screw body. The conductor has a first terminal at the proximal end and a second terminal at the distal end. The conductor and both of the terminals are electrically insulated from surrounding portions of the screw body. Accordingly, when the screw is driven into bone tissue and a stimulating current is applied at the first terminal, the current is directed substantially through the conductor to flow into tissue adjacent the second terminal at the distal end, without shunting by other tissue that surrounds the screw body.

According to another aspect of the invention, a surgical bone screw includes an elongate screw body having a screw head at a proximal end of the body, a screw tip at a distal end of the body, and a threaded portion on the circumference of the body. An electrically insulated coating is applied on the outer periphery of the screw body except at certain exposed portions on the screw head and the screw tip. Accordingly, when the screw is driven into bone tissue and a stimulating current is applied to an exposed portion on the screw head, the current is directed substantially within the screw body and flows into tissue adjacent an exposed portion on the screw tip, without shunting by other tissue surrounding the screw body.

For a better understanding of the invention, reference is made to the following description taken in conjunction with the accompanying drawing and the appended claims.

DETAILED DESCRIPTION OF THE INVENTION

Figure 2:
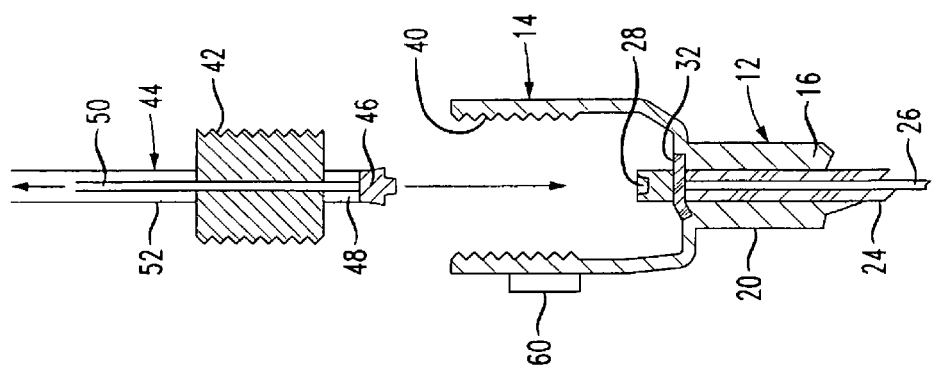
FIG. 2 is a view of a polyaxial head extension on the bone screw in FIG. 1, and a drive bit of a screw drive tool according to the invention.
Figure 1:
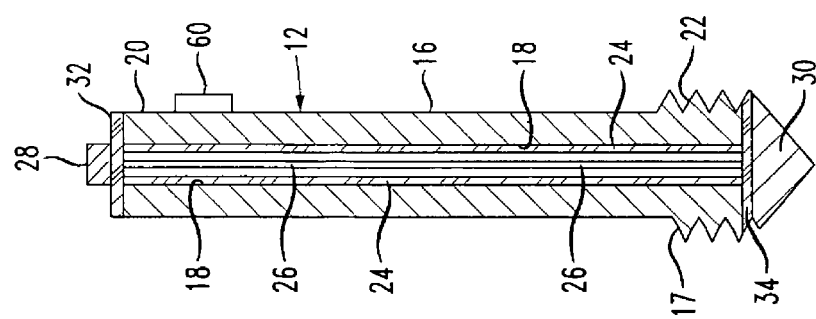
FIG. 1 is a sectional view of a first embodiment of a surgical bone screw according to the invention.

The inventive bone screw construction allows an electrical stimulating current applied at a proximal end of the screw to be channeled within the screw body, and to flow only into bone tissue that contacts a distal end of the screw while a surgeon drives the screw in place. FIG. 1 shows one embodiment of a bone screw 12 according to the invention. FIG. 2 illustrates details of a polyaxial head extension 14 that may be provided on the bone screw 12, and a matching drive tool 44, according to the invention.

The bone screw 12 includes an elongated screw body 16 that is cannulated, i.e., the screw body has a through passage 18 that extends between a proximal or head end 20 of the body 16, and a distal or tip end 22 of the body. A threaded portion 17 is formed on the circumference of the screw body, for example, in the region of the tip end 22 as shown in FIG. 1.

An electrical conductor 26 in the form of, e.g., a rod or wire is provided inside the passage 18. The conductor 26 is electrically insulated at 24 from the wall of the passage 18 by way of, e.g., an air gap, a plastics, and/or other known insulating substance to prevent electrical arcing between the conductor 26 and the passage wall while a stimulating current is carried by the conductor as explained below. The conductor 26 is terminated at a first terminal 28 at the head end 20 of the screw body 16, and at a second terminal 30 at the tip end 22 of the body.

Both of the terminals 28, 30 are also electrically insulated from surrounding portions of the screw body 16 by way of, e.g., corresponding insulating spacers 32, 34 that are seated or otherwise fixed at the head end 20 and at the tip end 22 of the screw body. The terminals 28, 30 are exposed on the outwardly facing sides of the spacers 32, 34, and the conductor 26 passes through and is supported by the spacers to avoid electrical contact or arcing between the conductor and surrounding portions of the screw body at the head and the tip ends 20, 22. It will be understood that the conductor 26 and its associated terminals 28, 30 may be formed integrally or as separate parts.

Accordingly, when a surgeon applies a stimulating current to the first terminal 28 as he or she drives the screw 12 into bone tissue, the current is channeled through the conductor 26 and flows directly into tissue adjacent the second terminal 30 at the tip end 22. Because the conductor 26 and the terminals 28, 30 are electrically insulated from the screw body 16, shunting of the current by other tissue surrounding the screw body, whether at the head or the tip end, is avoided.

Further, according to the invention, the terminal 28 may be disposed and formed for electrically contacting a drive bit of an associated screw drive tool, to which bit an electric potential is applied as the bit drives the screw into bone. See, e.g., the earlier mentioned U.S. Pat. Nos. 5,196,015 and 5,474,558, both of which are incorporated by reference. In such an application, it will be understood that the drive bit should be kept insulated in a known manner from conductive portions of the screw 12, other than the electrode 28.

FIG. 2 shows the polyaxial head extension 14 that may be provided at the head end 20 of the screw body 16. As generally known in the art, the extension 14 is cup shaped and an inside circumference 40 of the extension may be threaded or otherwise formed to engage a cylindrical retaining member 42 of an associated drive tool 44. The member 42 serves to hold the head end of a bone screw next to the tool's drive bit before the screw is firmly held by bone tissue.

FIG. 2 also shows a terminal 46 fixed at a distal end of a tool drive bit 48, wherein the terminal 46 is formed to contact the terminal 28 at the head end 20 of the bone screw 12 while the bit 48 is engaged with the head end. For example, an insulated electrical conductor 50 may be routed inside a drive shaft 52 of the tool 44 to the terminal 46, and an insulated spacer or other known means used to insulate the terminal 46 from adjacent portions of the drive bit 48. As disclosed in the mentioned '015 and '558 U.S. patents, the drive tool 44 may have an associated electrical potential source that can be switched to the electrode 46 through conductor 50 as desired, and, thus, cause a stimulating current to be applied to the terminal 28 on the screw 12.

If desired, the screw body 16 in FIG. 1 may have a commercially available RFID device or tag 60 fixed to a part (or embedded in a cavity) of the screw body 16. Alternatively, as shown in FIG. 2, the device 60 may be fixed to a part of the polyaxial head extension 14. In either case, the device 60 should preferably contain information concerning at least one of the screw size, the screw identification number, and the patient. Further, the screw drive tool itself may be provided with a commercially available RFID reader that is configured to read and to record the information contained in the device 60.

Figure 3:
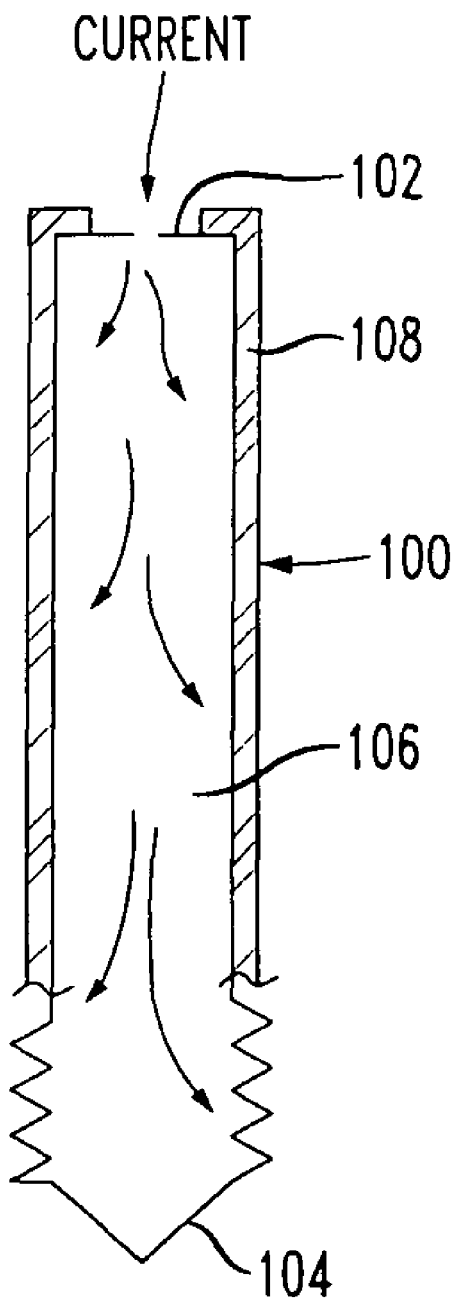
FIG. 3 is a sectional view of a second embodiment of a bone screw according to the invention.

FIG. 3 shows a second embodiment of a surgical bone screw 100 according to the invention. Except for exposed portions 102, 104 on the screw head and the screw tip, the metallic screw body 106 is coated with a commercially available, medically safe insulating substance 108 that prevents a stimulating current entering the exposed portion 102 on the screw head from leaking or otherwise flowing outside the screw into tissue surrounding the screw, except at the exposed portion 104 on the screw tip. The passage 18 and the conductor 26 provided in the embodiment of FIGS. 1 and 2, are therefore omitted in the embodiment of FIG. 3. The RFID device 60 in FIGS. 1 and 2 may, however, also be fixed on or within the bone screw 100 in FIG. 3, if desired.

Figure 4:
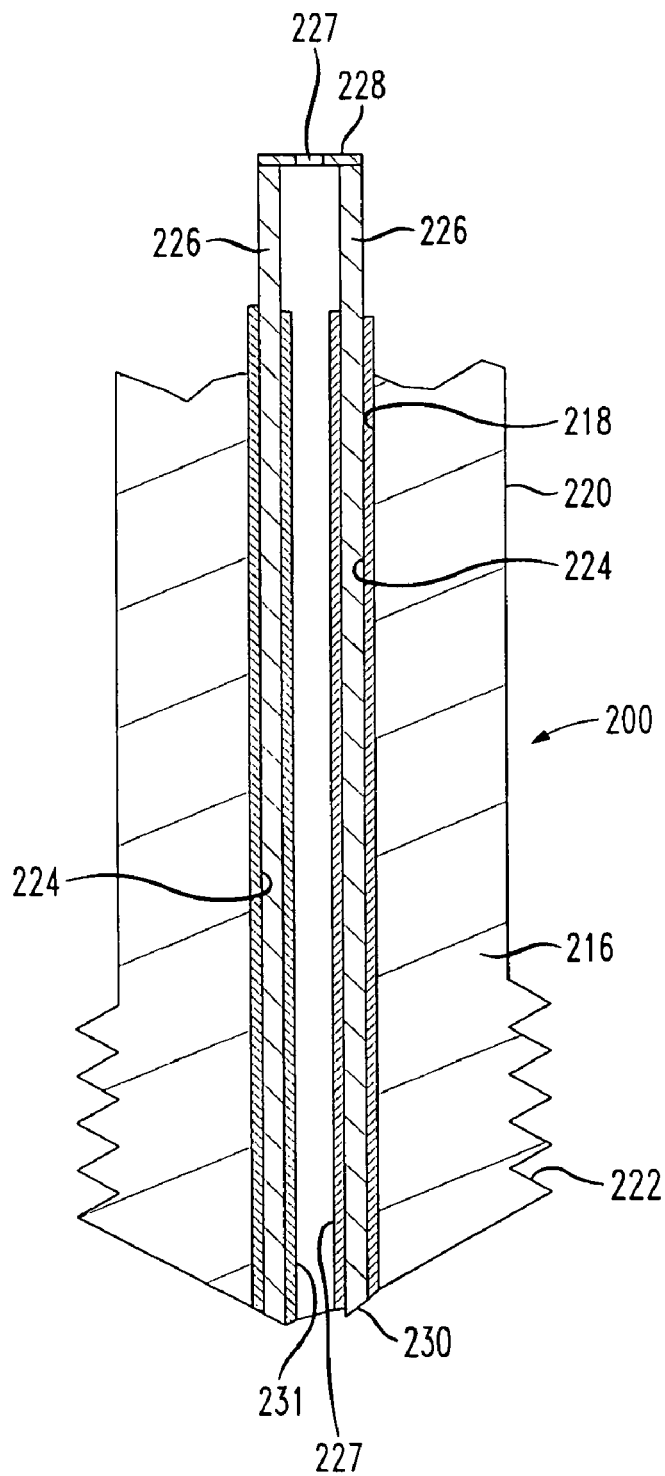
FIG. 4 is a sectional view of a third embodiment of a bone screw according to the invention.

FIG. 4 shows a third embodiment of a surgical bone screw 200 according to the invention. Components of screw 200 that may correspond to those of screw 12 in FIGS. 1 & 2, have corresponding reference numerals increased by 200.

The screw 200 has a screw body 216, wherein a passage 218 is formed over the length of the body between a head end 220 and a tip end 222. An electrical conductor 226 in the form of a tube extends through the passage 218, and the conductor is electrically insulated at 224 from the wall of the passage by way of, e.g., an air gap, a plastics, and/or other insulating substance to prevent electrical arcing between the conductor 226 and the passage wall. One end of the tubular conductor 226 is exposed at a first terminal 228 at the head end 220 of the screw body 216, and the opposite end of the conductor is exposed at a second terminal 230 at the tip end 222 of the body. If desired, an electrically insulated tube 231 may be adhered or otherwise secured on the inner circumference of the conductor 226. A passage 227 is thus formed that opens at the first and the second terminals 228, 230, and a guide wire can be passed through the passage 227 to facilitate placement of the screw 200 into a patient's bone.

Figure 5:
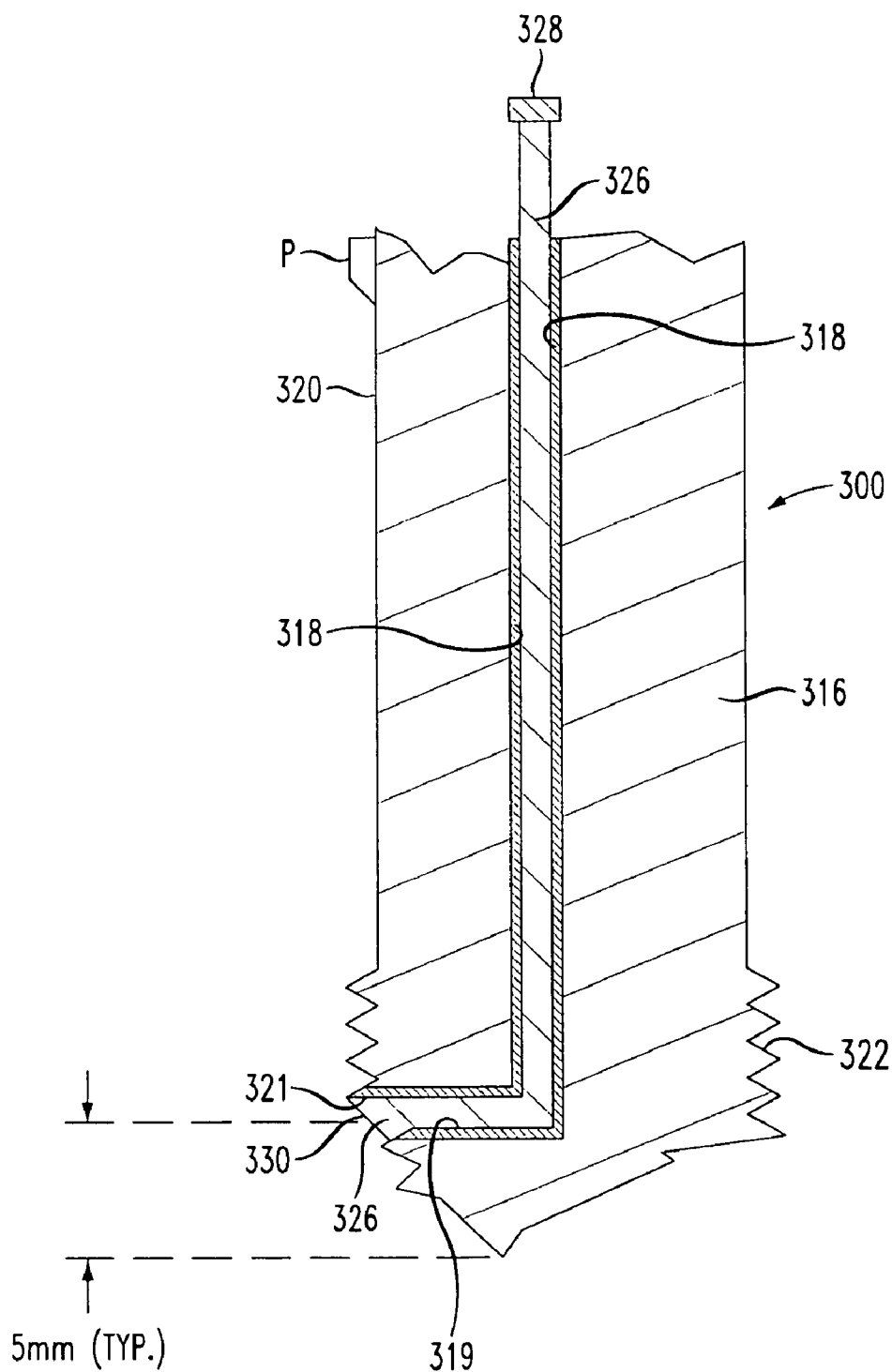
FIG. 5 is a sectional view of a fourth embodiment of a bone screw according to the invention.

FIG. 5 shows a fourth embodiment of a surgical bone screw 300 according to the invention. Components of screw 300 that may correspond to those of screw 12 in FIGS. 1 & 2, have corresponding reference numerals increased by 300. The screw 300 has a screw body 316 with a passage 318 one end of which opens at the head end 320 of the body. The passage 318 extends over the length of the body 316 to a point near the bottom tip of the screw 300, whereat the other end of the passage 318 communicates with one end of a lateral passage 319. The other end of the passage 319 opens at an exit point 321 on the circumference of the screw's tip end 322, wherein the exit point is, for example, about 5 mm from the bottom tip of the screw.

An insulated electrical conductor 326 extends continuously inside the passages 318, 319, between the open ends of the passages at which the conductor is exposed at corresponding terminals 328, 330. Thus, a stimulating current applied at the terminal 328 at the head end 320 of the screw body, is directed to flow into bone or other tissue adjacent the terminal 330 at the tip end 322 and at a certain position on the circumference of the tip end 322, rather than into tissue that is directly below the bottom tip of the screw. This construction therefore adds a directionality component to the stimulation process.

In particular, the head end of the screw 300 may be marked using, e.g., indicia, a raised pointer P, or other known means to identify a bearing with respect to the circumference of the screw at which the stimulating current is exiting the screw a known distance (e.g., 5 mm) from the screw's bottom tip. This information can be used by the surgeon to determine precisely where a breech has occurred in bone surrounding the screw 300 if a nervous reaction is monitored. For example, while the screw 300 is being driven into a vertebral pedicle and a stimulating current is applied to terminal 328 at the head end of the screw, the surgeon need only look down at the pointer P on the head end to know the bearing of the terminal 330 at the tip end of the screw deep in the pedicle. By slowly rotating the screw and monitoring patient response, the surgeon can confirm where a breech has occurred in the pedicle.

Figure 7:
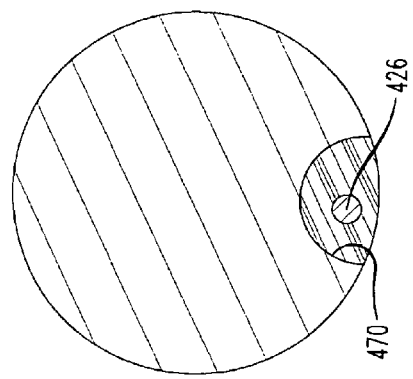
FIGS. 7 and 8 are sectional views of a fifth embodiment of a bone screw according to the invention.
Figure 8:
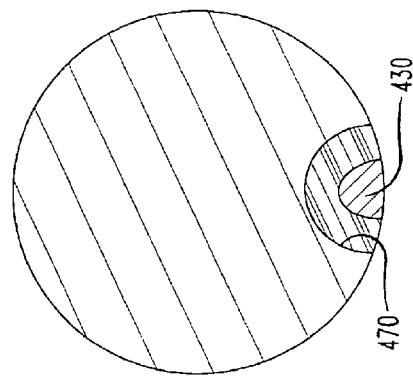
Figure 6:
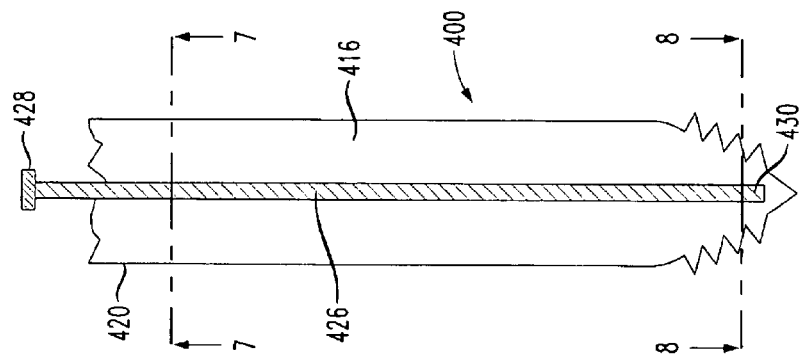
FIG. 6 is a side elevation view.

FIG. 6 is a side view, in elevation, of another embodiment of a surgical bone screw 400 according to the invention. FIG. 7 is a cross-sectional view of the screw 400 as taken along line 7-7 in FIG. 6, and FIG. 8 is a cross-sectional view of the screw 400 as viewed along line 8-8 in FIG. 6.

The screw 400 has a screw body 416 that may be either cannulated or non-cannulated, as desired, and still provide a directionality feature as in the embodiment of FIG. 5. That is, when a stimulating current is applied to a terminal 428 at a head end 420 of the screw, the current is channeled through an insulated conductor 426 to flow into bone or other tissue adjacent a terminal 430 a certain distance from the bottom tip of the screw, and in a known direction laterally of the screw. Specifically, a channel or groove 470 is cut in the outside circumference of the screw body 416 over the length of the screw and the insulated conductor 426 is embedded within the groove 470.

The proximal and the distal ends of the conductor 426 are exposed at the terminals 428, 430, to allow contact with a source of stimulating current at terminal 428, and to cause the current to flow into bone or other tissue adjacent the terminal 430. The conductor 426 may be embedded permanently in the groove 470 (e.g., with a suitable adhesive or cement), or arranged for removal by the surgeon once it is determined that the screw 400 has been properly implanted.

While the foregoing represents preferred embodiments of the invention, it will be understood by those skilled in the art that various modifications and changes may be made without departing from the spirit and scope of the invention, and that the invention includes all such modifications and changes as come within the scope of the following appended claims.

I claim:

1. A surgical bone screw, comprising:
    an elongate screw body having at least a shank portion having a proximal end, a distal end, a threaded portion, and a passage extending between the proximal and distal ends, the shank portion extending along a central longitudinal axis from the proximal end to the distal end, the shank portion having an external surface that is conductive along the shank portion, the shank portion having an upper terminal proximate the proximal end and a lower terminal proximate the distal end, the upper terminal being coaxial with the longitudinal axis, the upper terminal defining the uppermost portion of the shank portion and being accessible from a proximal direction along the longitudinal axis, the upper and lower terminals electrically isolated from the external surface;
    an electrical conductor disposed inside the passage and electrically connecting the first and second terminals;
    an insulation portion disposed inside the passage and around the electrical conductor;
    a first insulating spacer fixed at the proximal end of the shank portion such that the upper terminal is exposed on a first surface of the first spacer and the electrical conductor passes through the first spacer; and
    a second insulating spacer fixed at the distal end of the shank portion such that the lower terminal is exposed on a first surface of the second spacer and the electrical conductor passes through the second spacer, the insulation portion and the first and second spacers electrically insulating the first and the second terminals from surrounding portions of the screw body so that when the screw is driven into bone tissue and a stimulating current is applied to the first terminal the current is directed substantially through the conductor to flow into tissue adjacent the second terminal without shunting by other tissue that surrounds the screw body.

2. A bone screw according to claim 1, wherein the first terminal is formed and arranged to contact an electrical terminal associated with a drive bit.

3. A bone screw according to claim 1, including a radio frequency identifier (RFID) device fixed to a part of the screw body.

4. The bone screw of claim 3, wherein the RFID device is constructed and arranged to contain information concerning at least one of an associated screw size, a screw identification number, and a patient.

5. A bone screw according to claim 1, wherein the proximal end of the screw body includes a polyaxial head extension.

6. A bone screw according to claim 5, wherein the first terminal is formed and arranged to contact a terminal associated with a drive bit.

7. A bone screw according to claim 5, including a radio frequency identifier (RFID) device fixed to a part of the polyaxial head extension.

8. The bone screw of claim 7, wherein the RFID device is constructed and arranged to contain information concerning at least one of an associated screw size, a screw identification number, and a patient.

9. A bone screw according to claim 1, wherein the second terminal forms a bottom tip of the shank portion.

10. A bone screw according to claim 1, wherein the second terminal is disposed at a known angular position on the circumference of the distal end of the shank portion, and at a known distance from a bottom tip of the shank portion.

11. The bone screw of claim 10, including a marker on the circumference of the proximal end of the screw body, and the marker has an angular position corresponding to that of the second terminal on the circumference of the distal end of the screw body.

12. A bone screw according to claim 1, wherein the electrical conductor is in the form of a rod or wire.

13. A bone screw according to claim 1, wherein the electrical conductor is in the form of a tube.

14. A bone screw according to claim 1, wherein the insulation portion comprises an air gap.

15. A bone screw according to claim 1, wherein the insulation portion comprises a plastic.

16. A bone screw according to claim 1, wherein the first surface of the first spacer and the first surface of the second spacer are each outwardly facing sides that are transverse to the longitudinal axis.

17. A bone screw according to claim 1, wherein the first and second spacers each include a disk-like configuration.

18. A bone screw according to claim 1, wherein the conductor, the lower spacer is tapered.

19. A bone screw according to claim 1, wherein an inner surface of the insulation portion engages an outer surface of the electrical conductor.

20. A bone screw according to claim 1, wherein the threaded portion has a maximum diameter that is greater than a maximum diameter of the shank portion and a maximum diameter of a head of the screw body.

* * * * *